United States Patent [19]

Hagen et al.

[11] Patent Number: 5,072,001

[45] Date of Patent: Dec. 10, 1991

[54] CERTAIN OPTICALLY ACTIVE SUBSTITUTED 3-PYYROLIDINE ACETIC ACID DERIVATIVES USEFUL AS INTERMEDIATES

[75] Inventors: Susan E. Hagen, Canton Township, Wayne County; Mark J. Suto, Whitmore Lake, both of Mich.

[73] Assignee: Warner-Lambert Company, Morris Plains, N.J.

[21] Appl. No.: 621,101

[22] Filed: Nov. 30, 1990

[51] Int. Cl.$^5$ .......................................... C07D 207/08
[52] U.S. Cl. .................................. 548/572; 546/123; 546/156; 548/566; 548/567
[58] Field of Search ........................................ 548/572

[56] References Cited

U.S. PATENT DOCUMENTS 4,665,079  5/1987  Culbertson et al. ................ 514/312

Primary Examiner—Bernard Dentz
Attorney, Agent, or Firm—Ronald A. Daignault

[57] ABSTRACT

Optically pure isomers of 7-[3-(1,1-dialkylmethyl-1-amino)-1-pyrrolidinyl]quinolones and naphthyridones as therapeutically active and safe antibacterial agents are described, as well as pharmaceutical compositions thereof, and a method of treating bacterial infections therewith. Also described is a method of manufacture of the quinolones and naphthyridones as well as the starting materials, the optically pure pyrrolidine moieties for attachment at the 7-position.

4 Claims, No Drawings

CERTAIN OPTICALLY ACTIVE SUBSTITUTED 3-PYYROLIDINE ACETIC ACID DERIVATIVES USEFUL AS INTERMEDIATES

BACKGROUND OF THE INVENTION

The identification and selection of an antibacterial chemotherapeutic agent for development depends on several properties. These include in vitro potency against bacteria, in vivo efficacy in animals and man, pharmacokinetic parameters such as good plasma levels and favorable metabolism, and reduced side effects and toxicity. The ideal agent should have the best blend of these properties.

Within the quinolone/naphthyridone class of antibacterials, efforts are directed toward increasing in vitro and in vivo efficacy while lowering certain side effects such as phototoxicity and cytotoxicity and reducing general toxicity as well.

It is also known that within the chiral environment of living organisms, individual stereoisomers/enantiomers of drugs may show unique properties relative to the racemic mixtures. When this occurs, the optimal properties of the drug can only be obtained when the most favorable stereoisomer is utilized in its pure chiral form.

U.S. Pat. No. 4,665,079 shows quinolones and naphthyridines by structural formula to have 7-[3-(1-amino-1-alkylmethyl)-1-pyrrolidinyl] side chains. These compounds of formula A, where $R_1$ or $R_2$

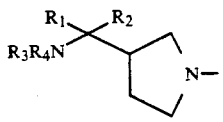

are alkyl or hydrogen were revealed to have good in vitro antibacterial potency. European Patent Publication 207,420 describes quinolones/naphthyridones substituted at $C_7$ with such compounds as A having the two asymmetric centers, and the preparation of two diastereomeric mixtures, each containing two nonseparable enantiomers. These mixtures are now known to consist of the formulas of mixture B and mixture C.

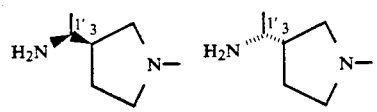

Mixture B

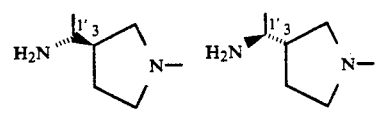

Mixture C

The mixtures B and C (of unknown composition) were described to possess improved in vivo activity relative to unsubstituted compounds (those of formula A where $R_1$ and $R_2$ are both hydrogen). All data reported were for the mixtures, and no method of separation of the mixtures was described. At the International Congress of Antimicrobial Agents and Chemotherapy (ICAAC) in Houston, Tex., 1989, there were reported certain individual enantiomers of 1-ethyl and 1-cyclopropyl-6,8-difluoroquinolone-3-carboxylic acids. The 3-(R)-1'(S) enantiomers were disclosed to have the most potent activity in vitro. One stereoisomer (3R,1'S) was shown to have improved in vivo efficacy relative to an unsubstituted compound (formula A where $R_1$ and $R_2$ are both hydrogen). Except for the in vitro data, no other comparisons among the pure stereoisomers were provided.

It has now been found that dialkylation (to be defined below) at the 1'-aminoethyl position of a 3-pyrrolidine substituent removes one asymmetric center and results in a group having only one asymmetric carbon atom and thus only two possible optical isomers instead of four isomers.

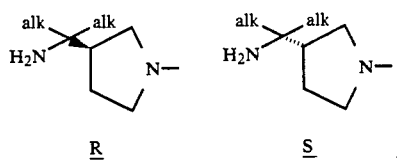

It has also been found that the removal of one asymmetric center greatly simplifies the synthesis, separation, and purification relative to pyrrolidine in B and C with two asymmetric centers. It has further been found that the R-(1,1-dialkylated-1-aminomethyl)pyrrolidine, when coupled at the 7-portion of a quinolone or naphthyridone leads to antibacterial agents with improved activity and safety, especially as to cytotoxicity.

SUMMARY OF THE INVENTION

Accordingly, the present invention includes an optical isomer of a compound of the formula I

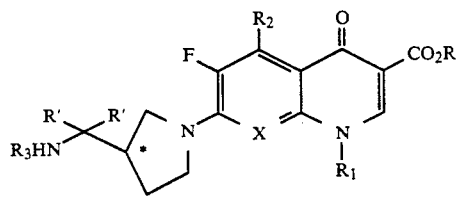

wherein * denotes an asymmetric carbon atom;
X is C—H, C—F, C—Cl, C—CF$_3$, C—OR" or N, in which R" is hydrogen or alkyl of 1 to 3 carbon atoms;
R is H, alkyl of 1 to 3 carbon atoms or a cation;
$R_1$ is cyclopropyl or 2,4-difluorophenyl;
$R_2$ is hydrogen, methyl or amino;
$R_3$ is hydrogen, alkyl of 1–3 carbon atoms or an amino protective group;
R' is alkyl of 1 to 3 carbon atoms; or a pharmaceutically acceptable acid addition salt thereof.

The preferred isomer has the R configuration.
Preferred R isomers are those of the formula II:

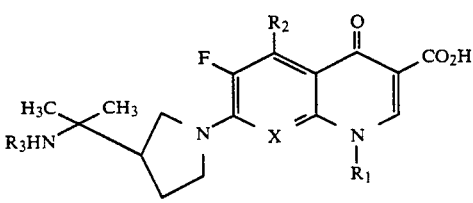

wherein $R_3$ is hydrogen or methyl.

Particularly valuable are the following:
- R-7-[3-(1-amino-1-methylethyl)-1-pyrrolidinyl]-1-cyclopropyl-6-fluoro-1,4-dihydro-4-oxo-1,8-naphthyridine-3-carboxylic acid,
- R-7-[3-(1-amino-1-methylethyl)-1-pyrrolidinyl]-8-chloro-1-cyclopropyl-6-fluoro-1,4-dihydro-4-oxo-3-quinolinecarboxylic acid,
- R-8-chloro-1-cyclopropyl-6-fluoro-1,4-dihydro-7-[3-[1-methyl-1-methylamino)ethyl]-1-pyrrolidinyl]-4-oxo-3-quinolinecarboxylic acid,
- R-7-[3-(1-amino-1-methylethyl)-1-pyrrolidinyl]-1-cyclopropyl-6-fluoro-1,4-dihydro-4-oxo-3-quinoline-carboxylic acid,
- R-5-amino-7-[3-(1-amino-1-methylethyl)-1-pyrrolidinyl]-1-cyclopropyl-6,8-difluoro-1,4-dihydro-4-oxo-3-quinolinecarboxylic acid,
- R-7-[3-(1-amino-1-methylethyl)-1-pyrrolidinyl]-1-cyclopropyl-1,4-dihydro-6-fluoro-8-methoxy-4-oxo-3-quinolinecarboxylic acid, R-5-amino-7-[3-(1-amino-1-methylethyl)-1-pyrrolidinyl]-1-cyclopropyl-6-fluoro-1,4-dihydro-8-methoxy-4-oxo-3-quinolinecarboxylic acid,
- R-7-[3-(1-amino-1-methylethyl)-1-pyrrolidinyl]-1-cyclopropyl-6-fluoro-1,4-dihydro-4-oxo-8-trifluoromethyl-3-quinolinecarboxylic acid,
- R-7-[3-(1-amino-1-methylethyl)-1-pyrrolidinyl]-1-(2,4-difluorophenyl)-6-fluoro-1,4-dihydro-5-methyl-4-oxo-3-quinolinecarboxylic acid,
- R-7-[3-(1-amino-1-methylethyl)-1-pyrrolidinyl]-1-(2,4-difluorophenyl)-6-fluoro-1,4-dihydro-4-oxo-1,8-naphthyridine-3-carboxylic acid,
- R-5-amino-1-cylopropyl-6,8-difluoro-1,4-dihydro-7-[3-[1-methyl-1-(methylamino)ethyl]-1-pyrrolidinyl]-4-oxo-3-quinolinecarboxylic acid,
- R-1-cyclopropyl-1,4-dihydro-6-fluoro-8-methoxy-7-[3-[1-methyl-1-(methylamino)ethyl]-1-pyrrolidinyl]-4-oxo-3-quinolinecarboxylic acid,
- R-5-amino-1-cyclopropyl-6-fluoro-1,4-dihydro-8-methoxy-7-[3-[1-methyl-1-(methylamino)ethyl]-1-pyrrolidinyl]-4-oxo-3-quinolinecarboxylic acid,
- R-1-cyclopropyl-6-fluoro-1,4-dihydro-7-[3-[1-methyl-1-(methylamino)ethyl]-1-pyrrolidinyl]-4-oxo-1,8-naphthyridine-3-carboxylic acid,
- R-1-cyclopropyl-6-fluoro-1,4-dihydro-7-[3-[1-methyl-1-(methylamino)ethyl]-1-pyrrolidinyl]-4-oxo-8-trifluoromethyl-3-quinolinecarboxylic acid,
- R-5-amino-7-[3-(1-amino-1-methylethyl)-1-pyrrolidinyl]-1-cyclopropyl-6-fluoro-1,4-dihydro-4-oxo-3-quinolonecarboxylic acid,
- R-1-(2,4-difluorophenyl)-6-fluoro-1,4-dihydro-5-methyl-7-[3-[1-methyl-1-(methylamino)ethyl]-1-pyrrolidinyl]-4-oxo-3-quinolinecarboxylic acid, and
- R-1-(2,4-difluorophenyl)-6-fluoro-1,4-dihydro-7-[3-[1-methyl-1-(methylamino)ethyl]-1-pyrrolidinyl]-4-oxo-1,8-naphthyridine-3-carboxylic acid.

The present invention also includes a pharmaceutical composition comprising an antibacterially effective amount of a compound according to formula I in admixture with a pharmaceutically acceptable carrier or diluent.

The present invention further includes a method of treating bacterial infections comprising administering to a host in need thereof a pharmaceutical composition containing a compound of formula I.

In a second aspect of the present invention, there includes novel intermediates used to prepare the individual optical isomeric side chains. The [3-(1,1-dialkylated)-1-aminomethylpyrrolidine] as well as the optically pure side chain itself. These include a compound of the formula

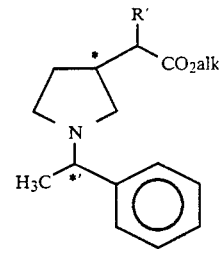

wherein * and *' are asymmetric carbon atoms having either the R or S configuration, and R' and alk are alkyl of 1-3 carbon atoms.

The second aspect also includes a compound of the formula

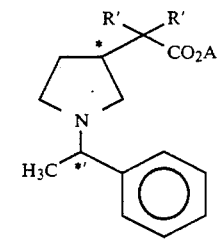

wherein * and *' are asymmetric carbon atoms having the R or S configurations;

R' is alkyl of 1-3 carbon atoms, and A is hydrogen or alkyl of 1-3 carbon atoms.

The second aspect further includes a compound of the formula

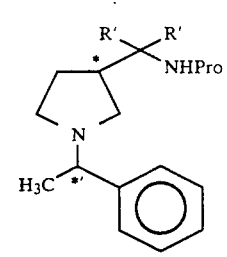

wherein * and *' are asymmetric carbon atoms having the R or S configurations; R' is alkyl of 1-3 carbon atoms, and Pro is an amino protecting group.

The second aspect especially includes the R or S isomer of the formula

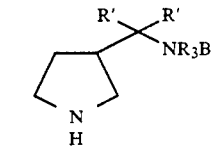

wherein R' is alkyl of 1-3 carbon atoms; $R_3$ is hydrogen or alkyl of 1-3 carbon atoms; and B is hydrogen or an amino protecting group (Pro).

A third aspect of the present invention is a process for the preparation of the R or S isomer of a compound of the formula

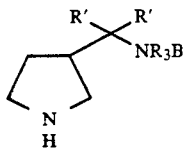

wherein B is a hydrogen or an amino protecting group; $R_3$ is hydrogen or alkyl from 1-3 carbon atoms, and R' is alkyl of 1-3 carbon atoms, comprising (a) dialkylating in a step-wise manner a compound of the formula

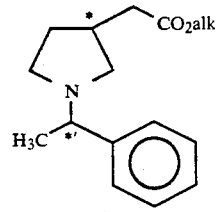

in which alk is alkyl of 1-3 carbon atoms, and * and *' are each either of the R or S configuration and wherein the first alkylation is carried out between about $-78°$ and about $-50°$ C. and the second between about $-20°$ and $+20°$ C.;

(b) removing the resulting ester (alk) of the formula

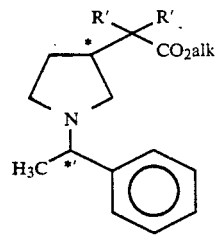

in which R' is alkyl of 1-3 carbon atoms by acid or base hydrolysis;

(c) undergoing the Curtius rearrangement of the resulting acid of the formula

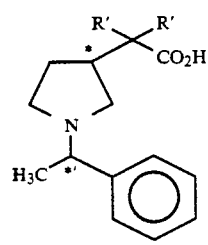

resulting in a compound of the formula

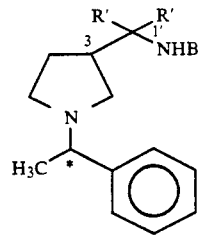

which, if desired, may be alkylated at the 1'-nitrogen by known means;

(d) removing the α-methylbenzyl group from the compound of the previous formula to give the desired product of the formula

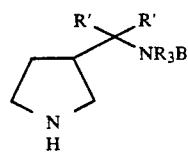

by catalytic hydrogenation.

Finally, the fourth aspect of the present invention is a method of using the R or S isomer of the formula

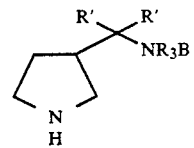

wherein R' is alkyl of 1-3 carbon atoms; $R_3$ is hydrogen or alkyl of 1-3 carbon atoms, and B is hydrogen or an amino protecting group which comprises reacting said R or S isomer with a compound of the formula

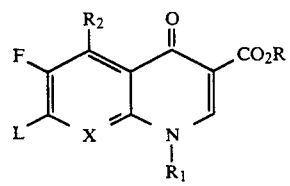

wherein X is C—H, C—F, C—Cl, C—$CF_3$, C—OR" or N, in which R" is hydrogen or alkyl of 1-3 carbon atoms; R is hydrogen, alkyl of 1-3 carbon atoms or a cation; $R_1$ is cyclopropyl or 2,4-difluorophenyl; $R_2$ is hydrogen, methyl or amino, and L is a leaving group and when B is an amino protecting group, removing said group by known means, e.g., hydrolysis or hydrogenation, to provide an antibacterial compound of the formula

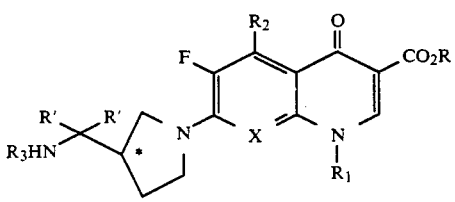

or a pharmaceutically acceptable salt thereof, wherein * is an asymmetric carbon atom having the R or S configuration, and $R_3$ is hydrogen or alkyl of 1-3 carbon atoms.

DETAILED DESCRIPTION

Groups having alkyl of 1 to 3 carbon atoms shown in the formula as R, R', $R_3$, alk or A includes methyl, ethyl, n-propyl or isopropyl; especially preferred is methyl.

An amino protecting group shown as Pro in the formulae includes known amino protecting groups capable of being removed easily either by hydrolysis or by catalytic hydrogenation. Easily hydrolyzable groups are, for example, t-butoxycarbonyl, carbobenzyloxy, and 4-methoxycarbobenzyloxy, and the like. Especially preferred is the t-butoxycarbonyl group.

Easily cleavable groups using catalytic hydrogenation, e.g., a noble metal catalyst such as palladium on carbon with hydrogen are, for example, benzyl, α-methylbenzyl, carbobenzyloxy, and the like.

The present invention is especially dependent on the synthesis of optically pure 3-(1,1-dialkylated-1-aminomethyl)pyrrolidines. These can be prepared as illustrated by the following schematic and description.

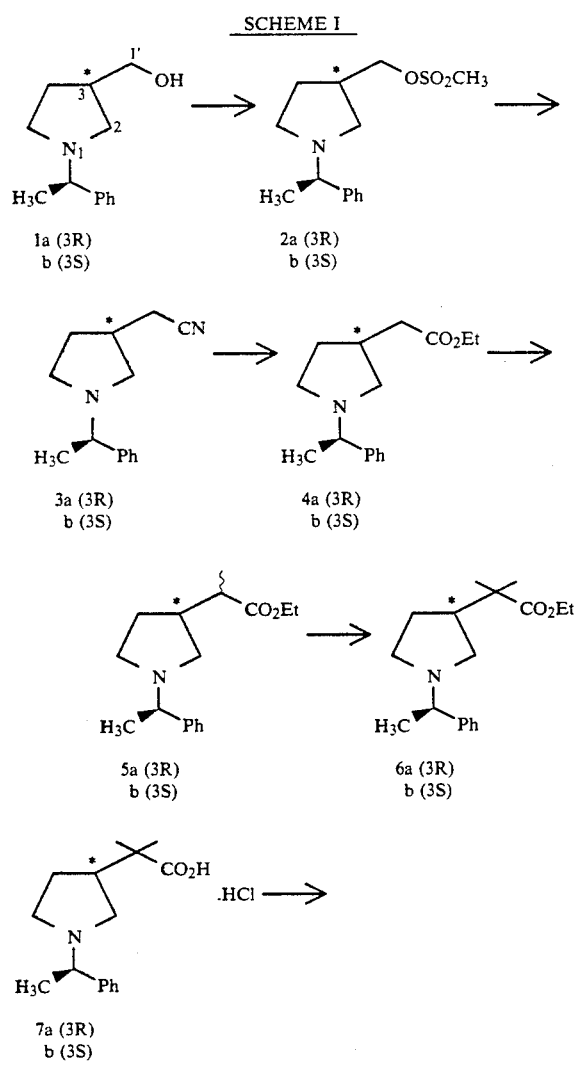

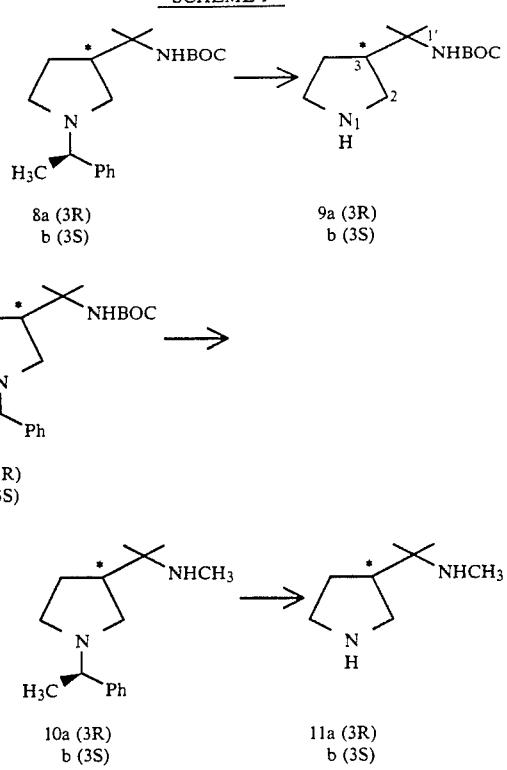

Compounds 1a and 1b were prepared essentially as described by Culbertson, et al (J. Med. Chem. 1987;30:1711). The yields were slightly improved particularly for 1b which was obtained in a yield > 90%. Compounds 3a and b were reported by L. Nielsen, et al (J. Med. Chem. 1990;33:71). Compounds 3a and b were obtained in yields of 84% and 57% after bulb to bulb distillation, by proceeding through the methanesulfonate followed by KCN/DMSO.

The esters, compounds 4a and b, were obtained by heating 3a and b in ethanol/$H_2SO_4$ at reflux.

The desired dialkylated esters 6a and b were obtained via stepwise alkylation of 4a and b. Treatment of 4 at between about −78° to −50° C. preferably at about −78° C. with lithium diisopropyl amide (LDA) followed by quenching with methyl iodide provided 5. Compound 6 was obtained using LDA once again but performing the reaction at between about −20° to about +20° C., preferably at about 0° C. Curtius rearrangement using diphenylphosphorylazide and t-butanol clearly provided 8, which was debenzylated under standard conditions, e.g., hydrogen and palladium on carbon catalyst at about room temperature and pressure (50-100 psi) to provide 9. The N-methyl analogues 11a and b were prepared via the lithium aluminum hydride reduction of 8a and b followed by debenzylation under standard conditions.

Proof of stereochemistry was done as described by Culbertson, et al (see above). The schematic diagram illustrates the use of (R)α-methylbenzyl as the protecting group for the pyrrolidine nitrogen as a preferred embodiment. The present invention also includes the use of either the R or S α-methylbenzyl analog and encompasses the use of other chiral protecting groups for the pyrrolidine nitrogen.

The pyrrolidines prepared were coupled to the appropriate quinolone or naphthyridine substrate by published procedures including; Domagala, et al, *J. Med. Chem.* 1988;31:503, Sanchez, et al, *J. Med. Chem.* 1988;31:983, Itawa, et al, European Patent Application 8702813.8, 1987, and British Patent 2,011,395A.

The enantiomeric quinolones and naphthyridines of the invention display potent antibacterial activity against gram-negative and especially gram-positive organisms both in vitro as well as in vivo. Their overall therapeutic advantages are also shown by including phototoxicity and cytotoxicity data as compared to a compound described in Example 13 of European Patent Publication 207,420.

The in vitro antibacterial activity is obtained when tested by the microtitration dilution method as described in Heifetz, et al., *Antimicr. Agents & Chemother.* 1974;6:124, which is incorporated herein by reference.

The in vivo activity is obtained when the compounds are tested according to the procedure of Miller, et al (*Proc. Soc. Exp. Biol. Med.* 1944;57:261). The median protective dose $PD_{50}$) was determined in mice given lethal systemic infections. Single doses of compound were given at time of challenge.

The phototoxicity data is obtained using depilated mice. Compound was administered orally each day for four successive days, followed each day by 3 hours of UVA radiation. The mice were examined for any positive signs (redness, erythema) relative to control animals. The no effect dose and the 50% effect dose were determined.

The cytotoxicity data is obtained using hamster V-79 cells. The cells were suspended in tissue culture medium and grown overnight. Cells were treated with drug for 3 hours, washed free of drug and then replated, and the colonies counted after 5 days. The concentration of drug that reduced colonies by 50% relative to control was recorded.

By use of the above methods, the following minimum inhibiting concentration values (MICs in $\mu$g/ml), $PD_{50}$'s in mg/kg, no effect phototoxicity dose in mg/kg and the cytotoxicity $IC_{50}$ in $\mu$g/mL were obtained for representative enantiomers of the invention and compounds of the prior art as shown in the table.

The in vivo data as $PD_{50}$'s are reported below the line of MICs for the same compound.

| Structure | Ent. clocae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox µg/ml |
|---|---|---|---|---|---|---|---|---|---|---|---|---|
| 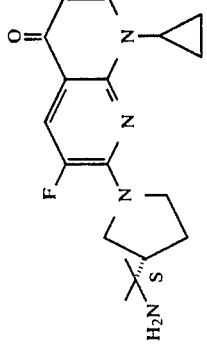<br>Example 3 | 0.2 | 0.2<br>10<br>3 | 0.4 | 0.8 | 3.1 | 0.1 | 0.025 | 0.1 | 0.05 | 0.1<br>32<br>7 | 30 | 58 |
| 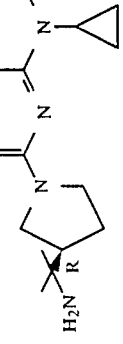<br>Example 4 | 0.1 | 0.05<br>5<br>1 | 0.2 | 0.4 | 1.6<br>50<br>22 | 0.05 | 0.003 | 0.05 | 0.006<br>5<br>2 | 0.013<br>4<br>1 | 30 | 130 |
| 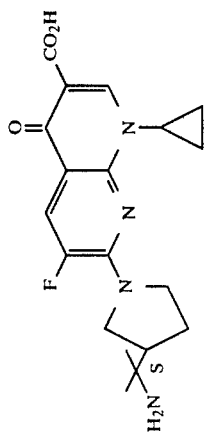<br>Racemic EP0207420<br>Example 13 | 0.1 | 0.1<br>6<br>2 | 0.2 | 0.4 | 1.6 | 0.05 | 0.013 | 0.05 | 0.025<br>10<br>3 | 0.025 | 30 | 66 |

-continued
| Structure | Ent. clocae MA2646 | Esch. coli Vogel | Klebs. pneumoniae MGH-2 | Prot. rettgeri M 1771 | Pseud. aeruginosa UI-18 | Staph. aureus H 228 | Staph. aureus UC-76 | Strep. faecalis MGH-2 | Strep. pneumoniae SV-1 | Strep. pyogenes C-203 | Photo NED mg/kg | Cytotox μg/ml |
|---|---|---|---|---|---|---|---|---|---|---|---|---|
| 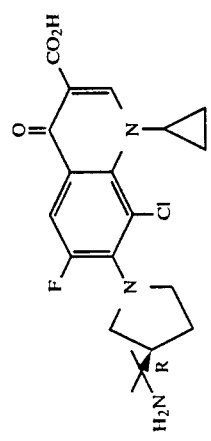<br>Example 1 | 0.1 | 0.1<br>27<br>4 | 0.2 | 0.4 | 1.6 | 0.025 | 0.013 | 0.05 | 0.013 | 0.025<br>13<br>4 | | |
| 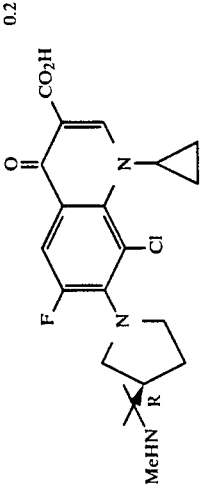<br>Example 2 | 0.05 | 0.05<br>8<br>1 | 0.1 | 0.2 | 0.8<br>100<br>17 | 0.006 | ≦0.003 | 0.013 | ≦0.003 | ≦0.003<br>2<br>0.14 | | |
| Example 6 | 0.2 | 0.2<br>11<br>2 | 0.4 | 0.4 | 3.1 | 0.013 | ≦0.003 | 0.025 | ≦0.003 | ≦0.003<br>3<br>0.5 | | |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The compounds of the invention can be prepared and administered in a wide variety of oral, parenteral and topical dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, Ph, etc.). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections, the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples are illustrative of the present invention.

PREPARATION OF STARTING MATERIALS

Example A (3R)-1-(R)-1-Phenylethyl]-3-(cyanomethyl)pyrrolidine

To a solution of (3R)-1-[(R)-1-phenylethyl]-3-(hydroxymethyl)pyrrolidine (25.2 g, 0.12 mol) in $CH_2Cl_2$ (250 mL) was added $Et_3N$ (18.8 mL, 0.13 mol). The mixture was cooled to 0° C. and treated dropwise with methanesulfonyl chloride (10.63 mL, 0.13 mol) dissolved in $CH_2Cl_2$ (125 mL). The mixture was stirred at 0° for 1.5 hours and then at 25° C. for 4 hours. Water was added and the organic layer was separated, washed with $NaHCO_3$ (2X), dried ($MgSO_4$) and concentrated to provide (3R)-1-[(R)-1-phenylethyl]-3-(methanesulfonyl methyl)-pyrrolidine (2a. 33.2 g); NMR ($CDCl_3$) δ 1.39 (m, 3H), 1.54 (m, 1H), 2.0 (m, 1H), 2.3–2.8 (m, 5H), 2.98 (d, 3H), 3.29 (q, 1H), 4.14 (t, 2H), 7.31 (m, 5H). The material was used directly in the next step.

A mixture of 2a (33.2 g, 0.12 mol) in DMSO (500 mL) was treated with KCN (16 g, 0.24 mol) and heated at 135°–140° for 18 hours. The reaction was cooled, poured into water (1600 mL) and extracted with $CHCl_3$. The organic layer was dried ($MgSO_4$) and concentrated. The residue was distilled (bulb to bulb) to provide the desired compound 3a (22.0 g, 84%); bp 40°–50°, 0.2 mm; NMR ($CDCl_3$) δ 1.35 (d, 3H), 1.40 (m, 1H), 2.0–2.8 (m, 9H), 3.1 (q, 1H), 7.2 (m, 5H); Analysis ($C_{14}H_{18}N_2$); Calcd.: C, 78.46; H, 8.47; N, 13.07. Found: C, 78.56, H, 8.41; N, 12.56.

Example B

Ethyl (3R)-1-[(R)-1-phenylethyl)pyrrolidine-3-acetate: 4a

To a mixture of EtOH (30 mL) and $H_2SO_4$ (15 mL) at 25° C. was added (3R)-1-[(R)-1-phenylethyl]-3-(cyanomethyl)pyrrolidine 3a (7.5 g, 35 mmol) in EtOH (5 mL). The solution was heated at reflux for 7 hours, cooled, and the volume reduced by approximately one-half under reduced pressure. The residue was made basic with NaOH and extracted with EtOAc. The organic layer was dried, concentrated, and the residue distilled (bulb to bulb) to provide 4a (6.7 g, 73%); bp 120°–130° C. (0.1–0.2 mm).

Example C (3S)-1-(R)-1-phenylethyl]-3-(cyanomethyl)pyrrolidine (3b)

This was prepared in a manner similar to 3a (Example A) in a yield of 57%; bp 110°–120° C. (0.3–0.4 mm bulb to bulb).

Example D

Ethyl (3S)-1-[(R)-1-phenylethyl]pyrrolidine-3-acetate (4b)

This was prepared in a manner similar to 4a (Example B) in a yield of 78%; bp 120°–130° (0.025 mm).

Example E

Ethyl (3R)-1-[(R)-1-phenylethyl]-pyrrolidine-3-(2-propionate) (5a)

To a solution of LDA (11.3 mmol) in THF (30 mL) at −78° C. was added a solution of (3R)-ethyl-1-[(R)-1-phenylethyl)pyrrolidine-3-acetate (4a) in THF (15 mL). The reaction was stirred at −78° C. for 45 minutes and methyl iodide (1.0 mL, 16.1 mmol) was added. The reaction was allowed to warm to 25° C. and stirring was continued for 1 hour. It was poured into saturated $NH_4Cl$ and extracted with EtOAc. The organic layer was dried ($MgSO_4$) and concentrated. The residue was filtered through silica gel (EtOAc) and the filtrates were concentrated to provide 5a (2.29 g, 91%); NMR ($CDCl_3$) δ 1.10–1.29 (m, 6H), 1.38 (d, 3H), 1.48 (m, 1H), 1.96 (m, 1H), 2.15 (m, 1H), 2.35–2.50 (m, 4H), 2.87 (m, 1H), 3.24 (m, 1H), 4.10 (q, 2H), 7.30 M, 5H); MS (M+1)=276.

Example F

Ethyl (3R)-1-[(R)-phenylethyl]pyrrolidine-3-[2-(2-methylpropionate)] (6a)

To a solution of LDA (25.2 mmol) in THF (50 mL) cooled to −78° C. was added a solution of ethyl (3R)-1-[(R)-phenylethyl]pyrrolidine-3-(2-propionate) in THF (50 mL) dropwise. After the addition was complete the reaction was warmed to 0° C. and stirred for 90 minutes. Then methyl iodide (2.6 mL, 41.8 mmol) was added, the mixture was allowed to warm to room temperature and stirred for 2 hours. The resulting suspension was poured into saturated $NH_4Cl$ and extracted with EtOAc. The organic layer was dried ($MgSO_4$) and concentrated to an oil. Chromatography over silica gel (9/1, $CHCl_3$/EtOAc) provided 6a (2.0 g, 83%); NMR ($CDCl_3$) δ 1.12 (d, 6H), 1.27 (t, 3H), 1.37 (d, 3H), 1.60 (m, 1H), 1.80 (m, 1H), 2.20 (m, 1H), 2.40–2.60 (m, 3H), 2.75 (m, 1H), 3.10 (m, 1H), 4.08 (q, 2H), 7.30 (m, 5H); MS (M+1)=290.

Example G

Ethyl (3S)-1[(R)-1-phenylethyl]pyrrolidine-3-(2-propionate) (5b)

This was prepared in a yield of 87% in a manner analogous to 5a (Example E). The material was purified by chromatography over silica gel (9/1; $CHCl_3$/EtOH); MS (M+1)=276.

Example H (3S)-Ethyl-1[(R)-1-phenylethyl]pyrrolidine-3-[2-(2-methylpropionate)] (6b)

This was prepared in a yield of 92% in a manner analogous to 6a (Example F); NMR ($CDCl_3$) δ 1.11 (s, 6H), 1.20 (5, 3H), 1.34 (d, 3H), 1.84 (m, 1H), 2.30 (m, 2H), 2.48 (m, 2H), 2.74 (m, 1H), 3.15 (q, 1H), 4.08 (q, 2H), 7.30 (m, 5H); MS (M+1)=290.

Example I (3R)-1-[(R)-1-phenylethyl]pyrrolidine-3-[2-(2-methylpropionic acid)] monohydrochloride (7a)

A solution of (3R)-ethyl-1-[(R)-1-phenylethyl]-pyrrolidine-3-[2-(methylpropionate)] (6a) in THF (3 mL) and 6M HCl (40 mL) was refluxed for 4 hours and then stirred at room temperature for 18 hours. The aqueous solution was washed with ether and then concentrated to a foam to provide 6a which was used directly in the next step; NMR ($CDCl_3$) δ 1.05 (m, 6H), 1.12 (s, 3H), 1.62 (m, 3H), 2.67–3.20 (m, 3H), 1.7–2.1 (m, 2H), 3.75 (m, 1H), 4.44 (m, 1H), 7.43 (m, 3H), 7.65 (m, 2H).

Example J (3R)-(1'-Methyl)-1'-t-butoxycarbonylaminoethyl)-1-[(R)-1-phenylethyl]pyrrolidine (8a)

To a solution of (3R)-1-[(R)-1-phenylethyl]-pyrrolidine-3-[-2-(2-methylpropionic acid)] monohydrochloride (7a) (3.50 g, 11.8 mmol) in t-butanol (180 mL) was added Et₃N (2.38 g, 23.6 mmol). The mixture was stirred at room temperature for 1 hour and then diphenylphosphoryl azide (2.5 mL, 11.6 mmol) was added dropwise. The mixture was refluxed for 18 hours, cooled, and concentrated. The residue was partitioned between $CHCl_3$ and $H_2O$. The organic layer was washed with 5% $NaHCO_3$, dried ($MgSO_4$), and concentrated to an oil. Chromatography over silica gel ($CHCl_3$/EtOAc 8/2) provided the desired 8a (1.8 g, 47%); NMR ($CDCl_3$) δ 1.18 (m, 3H), 1.27 (m, 3H), 1.35 (d, 3H), 1.48 (s, 9H), 1.86 (m, 2H), 2.15 (m, 3H), 2.56 (m, 1H), 3.12 (m, 2H), 7.33 (m, 5H); MS (M+1)=333.

Example K (3R)-(1'-Methyl-1'-t-butoxycarbonylaminoethyl)-pyrrolidine (9a)

A solution of (3R)-(1'-methyl-1'-t-butoxycarbonylaminoethyl)-1-[(R)-1-phenylethyl]pyrrolidine (8a) (0.43 g, 1.29 mmol), 20% Pd/C (0.25 g) and methanol was shaken in a hydrogen atmosphere for 21 hours. The catalyst was filtered through celite and the filtrate was concentrated to provide 9a (0.25 g, 86%) as an oil; NMR ($CDCl_3$) δ 1.21 (d, 6H), 1.42 (s, 9H), 1.60–2.01 (m, 3H), 2.71–3.30 (m, 4H).

Example L (3S)-1-[(1R)-Phenylethyl]pyrrolidine-3[-2-(2-methylpropionic acid)] monohydrochloride (7b)

This was prepared in an analogous manner to 7a (Example I) in a yield of ~98%; NMR ($CDCl_3$) δ 1.03 (d, 6H), 1.62 (d, 3H), 1.90 (m, 2H), 2.81 (m, 2H), 3.73 (m, 1H), 4.40 (m, 1H), 7.43 (m, 3H), 7.62 (m, 2H).

Example M (3S)-1'-Methyl-1'-t-butoxycarbonylaminoethyl)-1-[(R)-1-phenylethyl]pyrrolidine (8b)

This was prepared in a manner analogous to 8a (Example J) in a yield of 53%; NMR ($CDCl_3$) δ 1.29 (d, 6H), 1.27 (s, 9H), 2.20–2.70 (m, 5H), 3.27–5.80 (m, 2H), 4.01 (m, 1H), 7.32 (m, 5H).

Example N (3S)-(1'-Methyl-1'-t-butoxycarbonylaminoethyl)-pyrrolidine (9b)

This was prepared in a manner analogous to 9a in Example K. A yield of 96%; NMR ($CDCl_3$) δ 1.14 (d, 3H), 1.30 (d, 3H), 1.42 (s, 9H), 1.75 (m, 1H), 1.94 (m, 1H), 2.82–3.35 (m, 4H), 3.60 (m, 1H), 4.0 (bs, 2H).

Example O (3R)-1'-Methyl-1'-methylaminoethyl)-1-[(R)-1-phenylethyl]pyrrolidine (10a)

To a solution of 1.0 g (3.0 mmol) of (3R)-(1'-methyl-1'-t-butoxycarbonylaminoethyl)-1-[(R)-1-phenylethyl]-pyrrolidine (8A) in 50 mL of dry THF was added 1.14 g (30.0 mmol) of lithium aluminum hydride portionwise. The reaction mixture was refluxed for 90 minutes, then cooled to room temperature. The mixture was treated with 0.9 mL of water, 1.2 mL of 40% NaOH, and 4.2 mL of water. The solids were filtered and washed with ether, and the combined filtrate and washings were concentrated. The product was distilled (bulb to bulb) to give the title compound (0.62 g, 84%); bp 100°–110° C., 0.2 mm; NMR ($CDCl_3$) δ 0.95 (d, J=5.0 Hz, 6H), 1.35 (d, J=6.7 Hz, 3H), 1.5–1.8 (m, 4H), 2.2 (m, 2H), 2.3 (s, 3H, NCH₃), 2.5 (t, 1H), 2.8 (m, 1H), 3.2 (q, 1H), 7.3 (m, 5H).

Example P (3R)-(1'-Methyl-1'-methylaminoethyl)pyrrolidine (11a)

A solution of 0.51 g (2.1 mmol) of (3R)-(1'-methyl-1'-methylaminoethyl)-1-[(R)-1-phenylethyl]pyrrolidine (10a), 0.5 g of 20% Pd/C, and 100 mL of methanol was shaken in a hydrogen atmosphere for 19 hours. The catalyst was filtered through celite and the filtrate was concentrated to give 0.28 g (96%) of the title compound as a clear yellow oil; NMR ($CDCl_3$) δ 1.05 (d, J=2 Hz, 6H), 1.7 (m, 2H), 1.85 (m, 1H), 2.3 (s, 3H, NCH₃), 2.8 (t, 1H), 3.0 (m, 3H), 3.65 (bs, 2H).

Example 1

(S)-7-[3-(1-Amino-1-methylethyl)-1-pyrrolidinyl]-8-chloro-1-cyclopropyl-6-fluoro-1,4-dihydro-4-oxo-3-quinolinecarboxylic acid, monohydrochloride A solution of 0.70 g (3.07 mmol) of (3S)-(1'-methyl-1'-t-butoxycarbonylaminoethyl)-pyrrolidine (9b), 0.66 g (2.20 mmol) of 8-chloro-1-cyclopropyl-6,7-difluoro-1,4-dihydro-4-oxo-3-quinoline-carboxylic acid, 0.72 g (7.2 mmol) of triethylamine and 30 mL of acetonitrile was heated at reflux for 6 hours. The solvent was removed in vacuo and the residue was chromatographed on E. Merck silica gel (230–400 mesh) eluting with $CHCl_3$/MeOH (90:10) to give 0.95 g of the (S)-7-[3-(1-t-butoxycarbonylamino-1-methylethyl)-1-pyrrolidinyl]-8-chloro-1-cyclopropyl-6-fluoro-1,4-dihydro-4-oxo-3-quinolinecarboxylic acid as a yellow powder. NMR (DMSO-d₆); δ 8.80 (s, 1H, C₂H), 7.83 (d, 1H, C₅H), 6.6 (bs, 1H, NH-t-BOC), 4.35 (m, 1H, cyclopropyl), 3.65–3.90 (m, 2H), 3.50 (m, 1H), 3.35 (m, 1H), 2.95 (m, 1H), 2.0 (m, 1H), 1.8 (m, 1H), 1.38 (s, 9H, t-BOC), 1.25 (d, 6H, methyls), 1.02–1.28 (m, 4H, cyclopropyl).

A solution of 0.96 g (1.87 mmol) of the above compound in 5 mL of glacial acetic acid and 5 mL of 6.0M hydrochloric acid was stirred at room temperature for 2 hours and concentrated in vacuo. The residue was triturated with 20 mL of 2-propanol/ether (1:5) and the resulting solid was removed by filtration, washed with ether, and dried in vacuo to give 0.73 g of the title compound as a bright yellow solid, mp 220°–223° C.

Example 2

(R)-7-[3-(1-Amino-1-methylethyl)-1-pyrrolidinyl]-8-chloro-1-cyclopropyl-6-fluoro-1,4-dihydro-4-oxo-3-quinolinecarboxylic acid, monohydrochloride A solution of 0.71 g (2.37 mmol) of 8-chloro-1-cyclopropyl-6,7-difluoro-1,4-dihydro-4-oxo-3-quinolinecarboxylic acid, 0.70 g (3.07 mmol) of (3R)-(1'-methyl-1'-t-butoxycarbonylaminoethyl)pyrrolidine (9a), 0.72 g (7.2 mmol) of triethylamine and 20 mL of acetonitrile was heated at reflux for 7 hours. The solvent was removed in vacuo and the residue was chromatographed on E. Merck silica gel (230–400 mesh) eluting with $CHCl_3$/EtOH (90;10) to give 1.1 g of (R)-7-[3-(1-t-

Butoxycarbonylamino-1-methylethyl)-1-pyrrolidinyl]-8-chloro-1-cyclopropyl-6-fluoro-1,4-dihydro-4-oxo-3-quinolinecarboxylic acid as a yellow powder. NMR (DMSO-d$_6$); δ 8.79 (s, 1H, C$_2$H), 7.82 (d, 1H, C$_5$H), 4.36 (m, 1H, cyclopropyl), 3.84 (m, 1H), 3.72 (m, 1H), 3.51 (m, 1H), 3.38 (m, 1H), 2.88 (m, 1H), 1.91 (m, 1H), 1.75 (m, 1H), 1.37 (s, 9H, t-BOC), 1.25 (d, 6H, methyls), 0.88-1.22 (m, 4H, cyclopropyl).

A slurry of 1.04 g (2.05 mmol) of the above compound in 5 mL of tetrahydrofuran was treated portionwise with 3 mL of 12.0M hydrochloric acid (½ mL every 15 minutes) over 1.5 hours. The resulting solution was stirred at room temperature for an additional 1.5 hours and the solvent was removed in vacuo. The oily residue was triturated with 20 mL of 2-propanol/ether (1:5) and the resulting solid was removed by filtration, dissolved in water, filtered through a fiber glass pad to clarify, and lyophilized. The fluffy, yellow solid was filtered with the aid of 10 mL of acetonitrile, washed with ether, and dried in vacuo to give 0.56 g of the title compound, mp 225°-227° C.

Example 3

(S)-7-[3-(1-Amino-1-methylethyl)-1-pyrrolidinyl]-1-cyclopropyl-6-fluoro-1,4-dihydro-4-oxo-1,8-naphthyridine-3-carboxylic acid, monohydrochloride A solution of 0.39 g (1.39 mmol) of 7-chloro-1-cyclopropyl-6-fluoro-1,4-dihydro-4-oxo-1,8-naphthyridine-3-carboxylic acid, 0.35 g (1.53 mmol) of (3S)-(1'-methyl-1'-t-butoxycarbonylaminoethyl)pyrrolidine (9b), 0.46 g (4.6 mmol) of triethylamine and 20 mL of acetonitrile was stirred at reflux for 18 hours. The reaction mixture was cooled to 0° C. and the solid was removed by filtration, washed with acetonitrile, ether, and dried in vacuo to give 1.13 g of a white solid. The filtrate was concentrated to give an additional 0.95 g of white solid. The combined solids were chromatographed on E. Merck silica gel (230-400 mesh), eluting with CHCl$_3$/MeOH (90:10) to give 1.76 g of (S)-7-[3-(t-butoxycarbonylamino-1-methylethyl)-1-pyrrolidinyl]-1-cyclopropyl-6-fluoro-1,4-dihydro-4-oxo-1,8-naphthyridine-3-carboxylic acid; NMR (DMSO-d$_6$); δ 8.55 (s, 1H, C$_2$H), 7.95 (d, 1H, C$_5$H), 6.7 (bs, 1H, NH-t-BOC), 3.51-4.20 (m, 3H, 2 pyrrolidine+1 cyclopropyl), 2.95-3.11 (m, 3H), 2.0 (m, 1H), 1.9 (m, 1H), 1.17-1.37 (m, 19H, 5-BOC+methyls+cyclopropyl).

A solution of 0.78 g (1.64 mmol) of the above compound in 10 mL of glacial acetic acid and 15 mL of 6.0M hydrochloric acid was stirred at room temperature for 18 hours. The solvent was removed in vacuo and the golden, oily residue was triturated with 20 mL of 2-propanol/ether (1:4). The solid which developed was removed by filtration, washed with acetonitrile, ether, and dried in vacuo to give 0.51 g of the title compound, mp 280°-282° C.

Example 4

(R)-7-[3-(1-Amino-1-methylethyl)-1-pyrrolidinyl]-1-cyclopropyl-6-fluoro-1,4-dihydro-4-oxo-1,8-naphthyridine-3-carboxylic acid, monohydrochloride A solution of 1.24 g (4.39 mmol) of 7-chloro-1-cyclopropyl-6-fluoro-1,4-dihydro-4-oxo-1,8-naphthyridine-3-carboxylic acid, 1.2 g (5.25 mmol) of (3R)-(1'-methyl-1'-t-butoxycarbonylaminoethyl)pyrrolidine (9a), 1.33 g (13.2 mmol) of triethylamine and 35 mL of acetonitrile was heated at reflux for 18 hours. The solvent was removed in vacuo and the residue was chromatographed on E. Merck silica gel (230-400 mesh), eluting with CHCl$_3$/MeOH (90:10) to give 1.61 g of (R)-7-[3-(1-t-butoxycarbonylamino-1-methylethyl)-1-pyrrolidinyl]-1-cyclopropyl-6-fluoro-1,4-dihydro-4-oxo-1,8-naphthyridine-3-carboxylic acid. NMR (DMSO-d$_6$); δ 8.55 (s, 1H, C$_2$H), 7.93 (d, 1H, C$_5$H), 3.6-4.05 (m, 5H, 4 pyrrolidines+1 cyclopropyl), 2.9 (m, 1H), 2.05 (m, 1H), 1.85 (m, 1H), 1.39 (s, 9H, t-BOC), 1.10-1.31 (m, 10H, methyls+cyclopropyl).

A suspension of 1.50 g (3.16 mmol) of the above compound in 20 mL of 6.0M hydrochloric acid and 20 mL of glacial acetic acid was stirred at room temperature for 18 hours. The resulting solution was filtered through a fiber glass pad to clarify and the filtrate was concentrated in vacuo to a golden oil. The residue was triturated with 30 mL of 2-propanol/ether (1:5) and the resulting solid was removed by filtration, washed with ether, and dried in vacuo to give 0.95 g of the title compound as a white solid. NMR (DMSO-d$_6$); δ 8.58 (s, 1H, C$_2$H), 8.15 (bs, 2H, NH$_2$), 8.0 (d, 1H, C$_5$H), 3.6-4.1 (m, 5H, pyrrolidine+cyclopropyl), 2.55 (m, 1H), 2.1 (m, 1H), 1.9 (m, 1H), 1.32 (s, 6H, methyls), 1.05-1.2 (m, 4H, cyclopropyl).

Example 5

(R)-7-[3-(1-Amino-1-methylethyl)-1-pyrrolidinyl]-1-cyclopropyl-6-fluoro-1,4-oxo-3-quinolinecarboxylic acid, monohydrochloride A solution of 0.62 g (2.34 mmol) of 1-cyclopropyl-6,7-difluoro-1,4-dihydro-4-oxo-3-quinolinecarboxylic acid, 0.75 g (3.28 mmol) of (3R)-(1'-methyl-1'-t-butoxycarbonylaminoethyl)pyrrolidine (9a), 0.72 g (7.2 mmol) of triethylamine and 30 mL of acetonitrile was heated at reflux for 18 hours. The suspension was cooled to 0° C. and the solid was removed by filtration, washed with water, acetonitrile, ether, and dried in vacuo to give 0.62 g of (R)-7-[3-(1-t-butoxycarbonylamino-1-methylethyl)-1-pyrrolidinyl]-1-cyclopropyl-6-fluoro-1,4-dihydro-4-oxo-3-quinolinecarboxylic acid, which was used without further purification.

A solution of 0.61 g (1.29 mmol) of the above compound in 5 mL of 6.0M hydrochloric acid and 5 mL of glacial acetic acid was stirred at room temperature for 3.5 hours. The solution was concentrated to a greenish-yellow oil which was triturated with 20 mL of 2-propanol/ether (1:3) to give 0.42 g of the title compound as a bright yellow solid. NMR (DMSO-d$_6$); δ 8.44 (s, 1H, C$_2$H), 7.53 (1H, C$_5$H), 6.91 (d, 1H, C$_8$H), 3.40-3.62 (m, 5H, 4 pyrrolidines+1 cyclopropyl), 2.83 (m, 1H), 1.96 (m, 2H), 1.30-1.35 (d, 6H, methyls), 1.05-1.12 (m, 4H, cyclopropyls).

Example 6

(R)-8-Chloro-1-cyclopropyl-6-fluoro-1,4-dihydro-7-{3-[1-methyl-1-(methylamino)ethyl]-1-pyrrolidinyl}-4-oxo-3-quinolinecarboxylic acid, monohydrochloride A solution of 0.42 g (1.40 mmol) of 8-chloro-1-cyclopropyl-6,7-difluoro-1,4-dihydro-4-oxo-3-quinolinecarboxylic acid, 0.27 g (1.90 mmol) of (3R)-(1'-methyl-1'-methylaminoethyl)pyrrolidine (11a), 0.43 g (4.3 mmol) of triethylamine and 50 mL of acetonitrile was heated at reflux for 32 hours. The reaction was concentrated in vacuo and the residue was suspended in water. The pH was adjusted to 12.0 and the solution was filtered through a fiber glass pad to clarify. The filtrate was acidified to pH 2.0 with 6.0M hydrochloric acid, filtered, and the filtrate lyophilized. The residue was suspended in 10 mL of 12.0M hydrochloric acid and filtered. The filtrate was concentrated in vacuo and the residue was removed by filtration, washed with 2-propanol, ether, and dried in vacuo to give 0.22 g of the title compound, mp 270°–273° C.

We claim:

1. An optically active compound of the formula

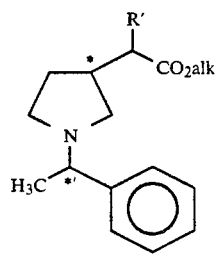

wherein * and *' are asymmetric carbon atoms having either the R or S configuration, and R' and alk are alkyl of 1 to 3 carbon atoms.

2. A compound according to claim 1, wherein * has the R configuration, and R' and alkyl are methyl.

3. An optically active compound of the formula

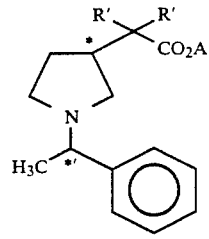

wherein * and *' are asymmetric carbon atoms having the R or S configurations;

R' is alkyl of 1 to 3 carbon atoms, and A is hydrogen or alkyl of 1 to 3 carbon atoms.

4. A compound according to claim 3, wherein * has the R configuration; R' is methyl, and A is hydrogen or methyl.

* * * * *

UNITED STATES PATENT AND TRADEMARK OFFICE
CERTIFICATE OF CORRECTION

PATENT NO. : 5,072,001
DATED : December 10, 1991
INVENTOR(S) : Hagen, et al

It is certified that error appears in the above-indentified patent and that said Letters Patent is hereby corrected as shown below:

On the title page: Item [54] Title: should read

CERTAIN OPTICALLY ACTIVE SUBSTITUTED 3-PYRROLIDEINE ACETIC
ACID DERIVATIVES USEFUL AS INTERMEDIATES

Signed and Sealed this

Thirteenth Day of July, 1993

Attest:

MICHAEL K. KIRK

*Attesting Officer*  *Acting Commissioner of Patents and Trademarks*